United States Patent
Peterman et al.

(10) Patent No.: US 10,941,437 B2
(45) Date of Patent: Mar. 9, 2021

(54) MOLECULAR MANIPULATION SYSTEM AND METHOD

(71) Applicant: AFS Technologies B.V., Amsterdam (NL)

(72) Inventors: Erwin Johannes Gerard Peterman, Amsterdam (NL); Gijs Jan Lodewijk Wuite, Amsterdam (NL); Gerrit Sitters, Amsterdam (NL); Douwe Kamsma, Amsterdam (NL)

(73) Assignee: AFS TECHNOLOGIES B.V., Amsterdam (NL)

( * ) Notice: Subject to any disclaimer, the term of this patent is extended or adjusted under 35 U.S.C. 154(b) by 562 days.

(21) Appl. No.: 14/898,112

(22) PCT Filed: Jun. 11, 2014

(86) PCT No.: PCT/NL2014/050377
§ 371 (c)(1),
(2) Date: Dec. 11, 2015

(87) PCT Pub. No.: WO2014/200341
PCT Pub. Date: Dec. 18, 2014

(65) Prior Publication Data
US 2016/0138095 A1     May 19, 2016

(30) Foreign Application Priority Data

Jun. 12, 2013 (NL) .................................. 2010960

(51) Int. Cl.
*C12Q 1/68* (2018.01)
*C12Q 1/6837* (2018.01)
(Continued)

(52) U.S. Cl.
CPC ....... *C12Q 1/6837* (2013.01); *G01N 29/0681* (2013.01); *G02B 21/32* (2013.01)

(58) Field of Classification Search
CPC ..... B01L 2300/0809; B01L 2400/0436; B01L 3/50273; B01L 3/502761;
(Continued)

(56) References Cited

U.S. PATENT DOCUMENTS 6,086,821 A * 7/2000 Lee .................. G01N 33/54373
204/157.42
6,216,538 B1 * 4/2001 Yasuda ................ B01D 21/283
210/748.05

(Continued)

FOREIGN PATENT DOCUMENTS

EP    1 615 061 A1    1/2006
JP    H09-292572 A    11/1997
(Continued)

OTHER PUBLICATIONS

Ding, et al., "On-chip manipulation of single microparticles, cells, and organisms using surface acoustic waves," *PNAS*, vol. 109, No. 28, pp. 11105-11109 (2012).
(Continued)

*Primary Examiner* — Betty J Forman
(74) *Attorney, Agent, or Firm* — Kilpatrick Townsend & Stockton LLP

(57) ABSTRACT

A molecular manipulation system for investigating molecules, having a sample holder constructed to hold a sample comprising a plurality of molecules attached on one side to a surface in the sample holder and on another side attached to a microbead of a plurality of microbeads. The system having; an acoustic wave generator to generate an acoustic wave exerting a force on the microbeads in the sample; and a detector device to detect a response of the plurality of microbeads in the sample on the force exerted by the acoustic wave to investigate the molecules attached to the microbeads.

14 Claims, 4 Drawing Sheets

(51) Int. Cl.
*G02B 21/32* (2006.01)
*G01N 29/06* (2006.01)

(58) Field of Classification Search
CPC ..... B01L 2200/0663; B01L 2300/0877; B01L 2400/0454; B01L 2400/0433; C12Q 1/6816; C12Q 2537/125; C12Q 2537/137; C12Q 1/6813; C12Q 1/6837; G01N 33/54306; G01N 29/0681; G01N 33/54366; G10K 15/00
See application file for complete search history.

(56) References Cited

U.S. PATENT DOCUMENTS

| | | | |
|---|---|---|---|
| 2001/0028497 A1 | 10/2001 | Uhl | |
| 2002/0076825 A1* | 6/2002 | Cheng | B01L 3/502761 436/174 |
| 2004/0086883 A1* | 5/2004 | Gaub | C12Q 1/6813 435/6.19 |
| 2007/0218534 A1* | 9/2007 | Klenerman | C07K 1/14 435/173.7 |
| 2009/0181463 A1* | 7/2009 | Chen | B01L 3/50857 436/150 |
| 2011/0207238 A1* | 8/2011 | Horii | B01L 3/50273 436/518 |
| 2011/0236957 A1* | 9/2011 | Weng | B82Y 15/00 435/235.1 |
| 2013/0034866 A1* | 2/2013 | Coleman | C07H 21/04 435/7.9 |
| 2013/0274119 A1* | 10/2013 | Knutson | G01N 33/5029 506/9 |

FOREIGN PATENT DOCUMENTS

| | | | | |
|---|---|---|---|---|
| WO | 94/18594 A1 | 8/1994 | | |
| WO | WO-2011149526 A2 * | 12/2011 | ......... | G01N 33/5029 |
| WO | 2013/051932 A1 | 4/2013 | | |

OTHER PUBLICATIONS

Glynne-Jones, et al., "Flexible Acoustic Particle Manipulation Device with Integrated Optical Waveguide for Enhanced Microbead Assays," *Analytical Sciences*, vol. 25, pp. 285-291 (2009).

Lilliehorn, et al., "Dynamic arraying of microbeads for bioassays in microfluidic channels," *Sensors and Actuators B*, vol. 106, pp. 851-858 (2005).

International Search Report for International Application No. PCT/NL2014/050377 dated Sep. 29, 2014.

* cited by examiner

MOLECULAR MANIPULATION SYSTEM AND METHOD

CROSS-REFERENCES TO RELATED APPLICATIONS

This application is a National Stage of International Application No. PCT/NL2014/050377, filed Jun. 11, 2014, and which claims the benefit of Netherlands Patent Application No. 2010960, filed Jun. 12, 2013, the disclosures of which are incorporated herein by reference.

The invention relates to a molecular manipulation system for investigating molecules, the system comprising:

a sample holder constructed for holding a sample comprising a plurality of (bio)molecules attached on one side to a surface in the sample holder and on another side attached to a microbead of a plurality of microbeads; and, a molecular manipulation device for manipulating the molecules by exerting a force on the microbeads.

The ability to observe the properties of molecules may be a great tool in biology, chemistry and physics. Early methods relied on electronic signals such as the patchclamp and electron microscopy. With the discovery of the green fluorescence protein (GFP), single biomolecules at work may be visualized in both in vitro and in vivo. A whole field of single molecule biophysics has emerged, dedicated to exploring the physical details of the cell at one molecule at a time. These single molecule experiments have helped us to create insight into the molecular structure and mechanism of protein folding, motor proteins, and DNA and protein interactions.

In order to learn about the physical properties of molecules, only observing may not be enough, often physical manipulation of the biomolecule of interest can yield additional information. Several techniques allow the manipulation by applying forces to the molecule, such as atomic force microscopy (AFM), and magnetic and optical tweezers. Each of these techniques has its own advantages and drawbacks. For example, in most of these techniques only one molecule is manipulated at the time.

It may be beneficial to manipulate a plurality of single molecules and investigate their behaviour. WO2013/051932 therefore discloses a molecular manipulation apparatus for investigating molecules attached on one side to a surface of a sample and on another side to a microbead. The apparatus having a radiation system for providing a radiation beam with a radiation intensity to the sample and the surface of the sample is transmissive for the radiation. The apparatus is provided with a sample holder for holding the sample with its transmissive surface in the beam of radiation such that the plurality of microbeads are pushed by the radiation. The radiation may have a power between 1 MilliWatt and 1 KiloWatt and a wavelength between 150 and 1500 nm. The apparatus has a detector for detecting a 3D position of the microbeads; and, a computer programmed for calculating a physical property of the molecules as a function of the 3D position of the plurality of microbeads.

It is an objective of the invention to provide an improved molecular manipulation system for investigation of a plurality of molecules.

According to an embodiment there is provided a molecular manipulation system for investigating molecules, the system comprising:

a sample holder constructed for holding a sample comprising a plurality of molecules attached on one side to a surface in the sample holder and on another side attached to a microbead of a plurality of microbeads; and, a molecular manipulation device for manipulating the molecules by exerting a force on the microbeads;

wherein the molecular manipulation device comprises an acoustic wave generator to generate an acoustic wave exerting a force on the microbeads in the sample.

The force exerted by the acoustic wave on a microbead may be between 0.1 to 1000 piconewton which is much larger than possible with a laser beam using the same powers. The acoustic waves do not provided a large heat load on the sample as the radiation of the laser may do when applying pushing with the radiation of the laser beam. The heat load may damage the molecules in the sample or may disturb the detector which is not the case if acoustic waves are provided according to the embodiment.

According to an embodiment the manipulation system comprises a detector device to detect a response of the plurality of microbeads in the sample on the force exerted by the acoustic wave to investigate the molecules attached to the microbeads. The effects of the manipulation of the plurality of molecules may therewith be investigated.

According to an embodiment the acoustic wave generator has an adjustable frequency to tune the frequency of the acoustic wave to a frequency of an acoustic standing wave. The frequency of the acoustic standing wave is determined by the dimensions of the sample. By having an adjustable frequency the frequency of the acoustic wave may be tuned to the (un)known frequency of the acoustic standing wave. The acoustic standing wave is resonating within the sample holder and thereby exerting a larger force. The force may be a factor more than 100,000 larger than the force of a normal not resonating acoustic wave.

According to an embodiment the system is constructed and arranged to have the surface in the sample holder perpendicular to the propagation direction of the standing wave generated with the acoustic wave generator. By this construction the molecules attached to the surface will receive a force stretching the molecules in a direction parallel to the propagation direction of the acoustic wave.

According to an embodiment the acoustic wave generator has a vibration actuating plane perpendicular to the propagation direction of the standing wave, the system being constructed and arranged to have the vibration actuation plane substantially parallel to the surface in the sample holder. By this construction the molecules attached to the surface and microbeads will receive a force stretching the molecules in a direction parallel to the propagation direction of the acoustic wave.

According to an embodiment the acoustic wave generator is a piezo element. The piezo may be controlled by an alternating current of a power source to create an acoustic standing wave. Piëzo element's are relatively cheap and may have a fast response time to adjust the force.

According to an embodiment the sample holder comprises a flow cell having a channel with the surface being along the inside of the channel. The molecules and/or microbeads may be provided by flowing them through channel of the flow cell.

According to an embodiment the sample holder comprises a container holder for holding a container with the surface provided with the sample perpendicular to the propagation direction of the standing wave. The container with the sample may simply be exchanged from the system in this way.

According to a further embodiment the detector device comprises a microscope, and the system is constructed and arranged to have a focal plane of the microscope substantially parallel and slightly above the surface provided with the sample to detect the microbeads attached with the molecules to the surface. The microscope provides an easy way to detect the microbeads. Preferably, air is present between the microscope and the sample.

According to an embodiment the microscope is provided with a detector to produce a digital image of the focal plane and the system is provided with a calculation device to calculate a position of the microbeads in a direction perpendicular to the focal plane by processing of an interference pattern caused by microbeads which are not in focus. By having a sensor producing a digital image the position of the microbeads may be digitally calculated.

According to an embodiment the microscope is provided with a detector to produce a digital image of the focal plane and the system is provided with a calculation device to calculate a position of the microbeads in a direction parallel to the focal plane.

According to an embodiment the microscope is provided with a detector to produce a digital image of the focal plane and the system is provided with a processing device to provide a quantitative analysis of the microbeads in the sample. Quantitative analyses may be useful if, for example it is necessary to determine a concentration of a particular molecule in the sample or for example it is necessary to extract quantitative physical information of a particular molecule in the sample.

According to an embodiment the system comprises an illumination system for illuminating the sample in the sample holder. Illuminating the sample improves imaging of the microbeads. A reflector may be provided in the system to reflect the radiation of the illuminator towards the sample.

According to an embodiment the acoustic wave generator has an adjustable frequency to tune the frequency of the acoustic wave to one of the resonating frequencies of the acoustic standing wave. When the frequency is set to a resonating frequency where pushing is not favorable this may result in acoustic streaming of the liquid in the sample. This may be helpful in the process of connecting the molecules to the surface and on connecting the microbeads to the molecules and the mixing of the fluids in the sample.

According to an embodiment the molecular manipulation system is provided with a reflector for illumination of the beads. The reflector being provided between the sample and the molecular manipulation device. By providing the illumination from the other side of the acoustic wave generator the reflector reflects the illumination back to the sample.

According to an embodiment the sample holder and the manipulation device are provided as a single unit. The manipulation system may function as a lab on chip giving it a very versatile use.

According to an embodiment there is provided a method of investigating molecules comprising:

providing a plurality of molecules to a sample in a sample holder;

connecting the molecules with one side to a surface in the sample holder and with another side to an individual microbead of a plurality of microbeads;

generating an acoustic wave with an acoustic wave generator to exert a force on the microbeads manipulating the molecules in the sample; and, detecting a response of the plurality of microbeads in the sample on the force exerted by the acoustic wave with a detector device to investigate the molecules attached to the microbeads.

According to an embodiment the microbeads are made of thermoplastics, thermosetting polymers or silica. The force exerted by the acoustic standing wave scale with the third power of the radius. Therefore the size is an important factor in the manipulation. No magnetic material is required in the microbeads which would be the case if a magnetic force is used. The microbeads made of thermoplastics, thermosetting polymers or silica are easy to produce and relatively cheap.

According to an embodiment the method comprises providing an additional molecule in the sample and detecting a response of the plurality of microbeads in the sample comprises detecting an influence of the additional molecules on the molecules attached to the microbeads. The manipulation system may be used to determine the influence of additional other molecules on the molecule under investigation. If the other molecules are provided they may have influence on for example the length of the molecule under investigation or the strength with which the molecule under investigation is attached, which may be measured with the manipulation system.

Embodiments of the invention will now be described, by way of example only, with reference to the accompanying schematic drawings in which corresponding reference symbols indicate corresponding parts, and in which.

Figure 3:
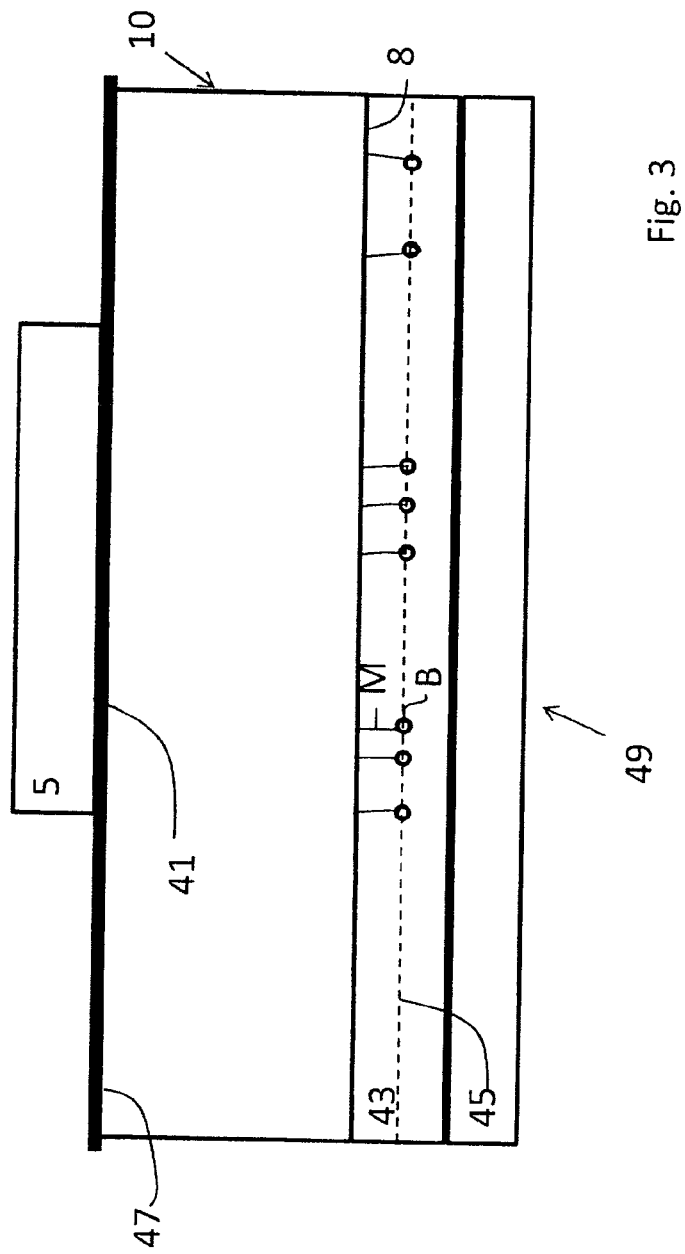
Figure 4A:
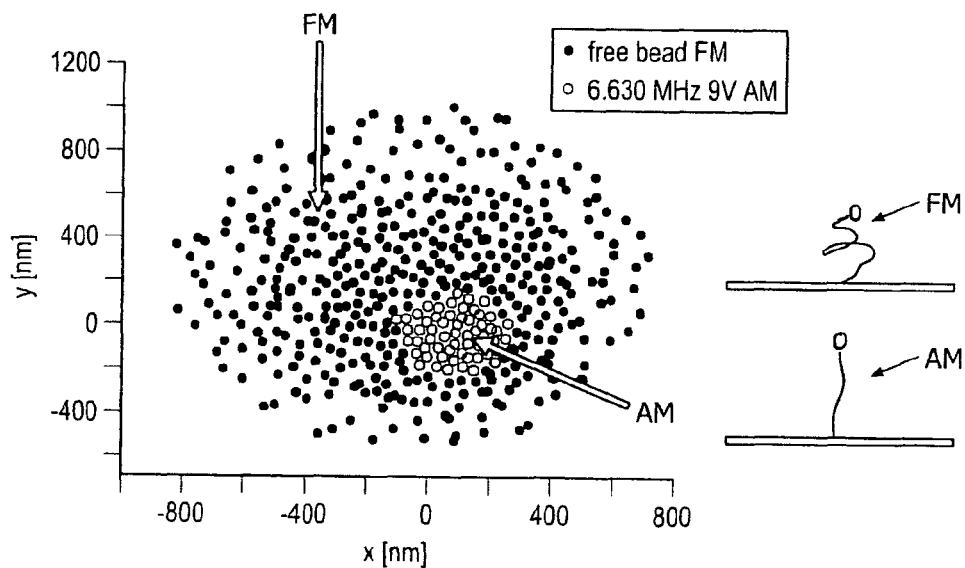
Figure 4B:
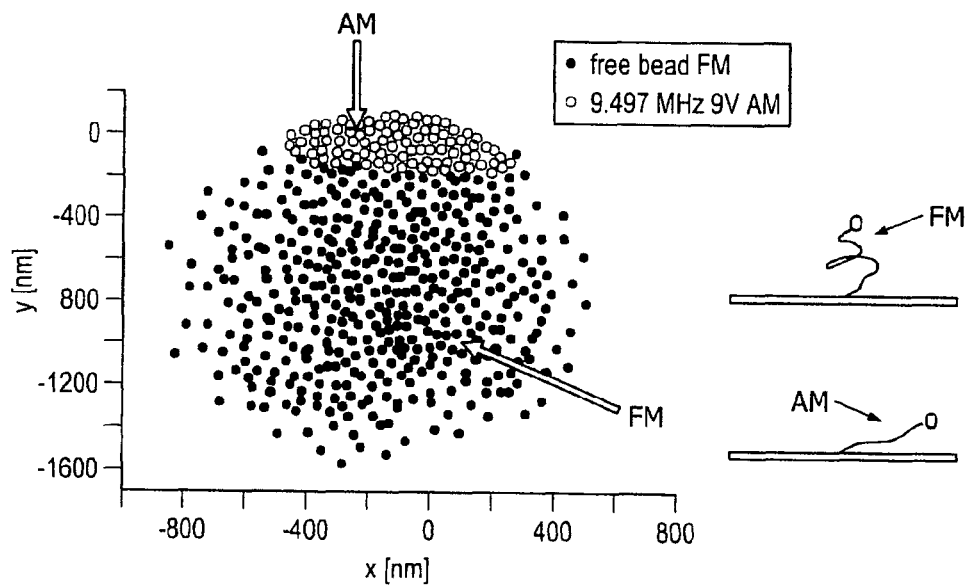

FIG. 3 discloses a molecular manipulation system according to an embodiment of the invention;

FIG. 4a depicts the X, Y movements of the microbeads when the microbeads are freely moving and with a 6.630 MHz acoustic standing wave (FIG. 4a); and, FIG. 4b depicts the X, Y movements of the microbeads FM when the beads are freely moving and when an acoustic wave of 9.567 MHz is provided a resonance frequency where streaming is favorable, thereby providing streaming in the flow channel.

Figure 1:
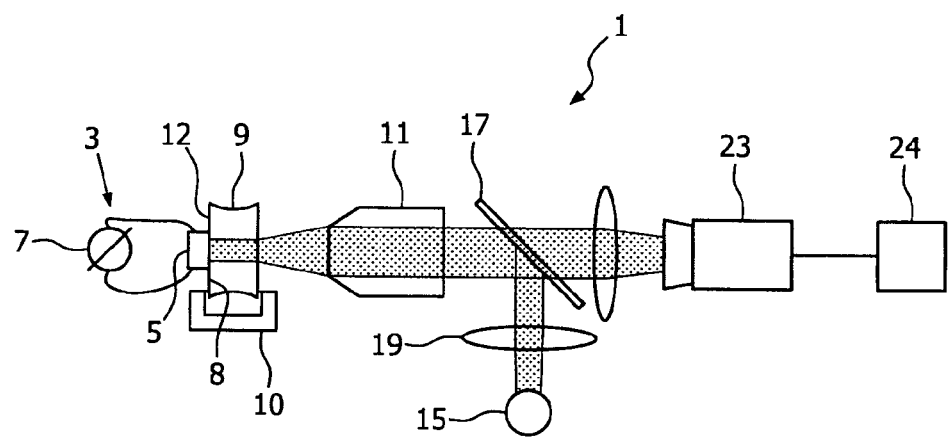
FIG. 1 depicts a schematic drawing of the molecular manipulation apparatus according to an embodiment.

FIG. 1 depicts a schematic drawing of the molecular investigation system 1 for investigating molecules according to an embodiment. A molecular manipulation device 3 may be provided with an acoustic wave generator 5, a transducer (e.g. a piezo element or a voice coil actuator) connected with a power source 7 for generating an acoustic wave. A sample 9 comprising a plurality of molecules attached on one side to a first surface 8 in the sample holder 10 and on another side attached to a microbead of a plurality of microbeads may be held by a sample holder 10 with its second surface 12 against the acoustic wave generator 5.

The power source 7 may provide an alternating current with an adjustable frequency to tune the frequency of the acoustic wave between 0 to 20 MHz to a frequency of an acoustic standing wave. The Voltage of the power source 7 may also be tuned to adjust the amplitude of the acoustic wave. The acoustic standing wave is resonating within the sample holder and thereby exerting a larger force. The force may be a factor more than 100,000 larger than the force of a normal not resonating acoustic wave. The force of the acoustic wave on a microbead may be between 0.1 to 1000 piconewton, preferably between 1 to 100 piconewton. The acoustic standing wave created over the flowcell will push the beads that are in this flowcell to the nod of the standing wave.

The adjustable frequency of the acoustic wave may be tuned to a resonance frequency of the acoustic standing wave, where streaming dominates, so as to create a streaming in the fluid of the sample, to mix the sample. A resonance frequency of the standing wave, where pushing is less favorable, will create mixing in the sample. This may be helpful in the process of connecting the molecules to the surface and on connecting the microbeads to the molecules.

The sample 9 may be held by a sample holder 10 with its second surface 12 against the acoustic wave generator 5. A microscope objective 11 may be used in the detector device for imaging an image of the microbeads on the detector 23. The objective is, preferably, of the air type, i.e. air is present between the objective 11 and the sample to insulate the vibrations in the sample from the microscope objective 11 such that the forces exerted by the standing wave are maximized and no vibrations are vibrating the objective.

Illumination of the sample 9 may be accomplished by an illumination system provided with a light source e.g. LED 15 and illuminator lens 19. The illumination beam may be coupled into the microscopic objective 11 using in-coupling optics, for example a beam splitter 17. The illumination beam may illuminate the sample 9. A reflector may be provided between the sample 9 and the acoustic wave generator 5 to reflect the illumination beam back towards the detector 23.

The light collected by the objective 11 may be imaged on the detector 23, for example a CMOS camera. The CMOS camera may be operable connected to a computer 24 for analyzing the image and/or calculating a physical property of the molecule. The computer 24 may be programmed to:

calculate a 2D position of the microbeads in the focal plane;

calculate a position of the microbeads in a direction perpendicular to the focal plane by processing of an interference pattern caused by microbeads which are not in focus;

calculate a position of the microbeads in a direction parallel to the focal plane; and/or, provide a quantitative analysis of the microbeads in the sample.

Figure 2A:
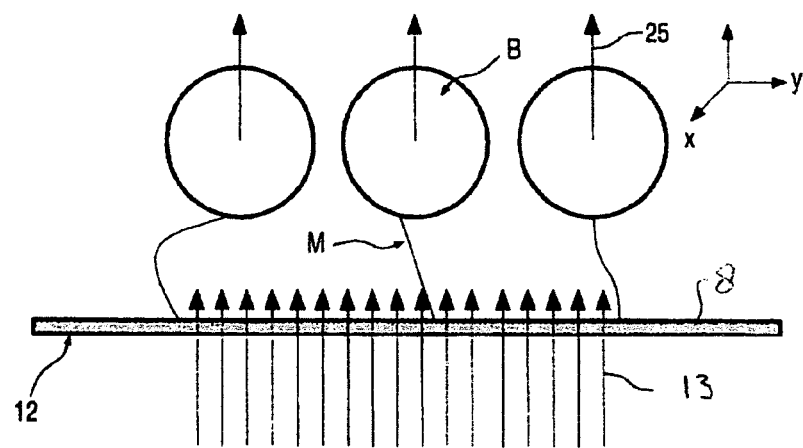
FIGS. 2a and 2b depict how the molecular manipulation apparatus is working.
Figure 2B:
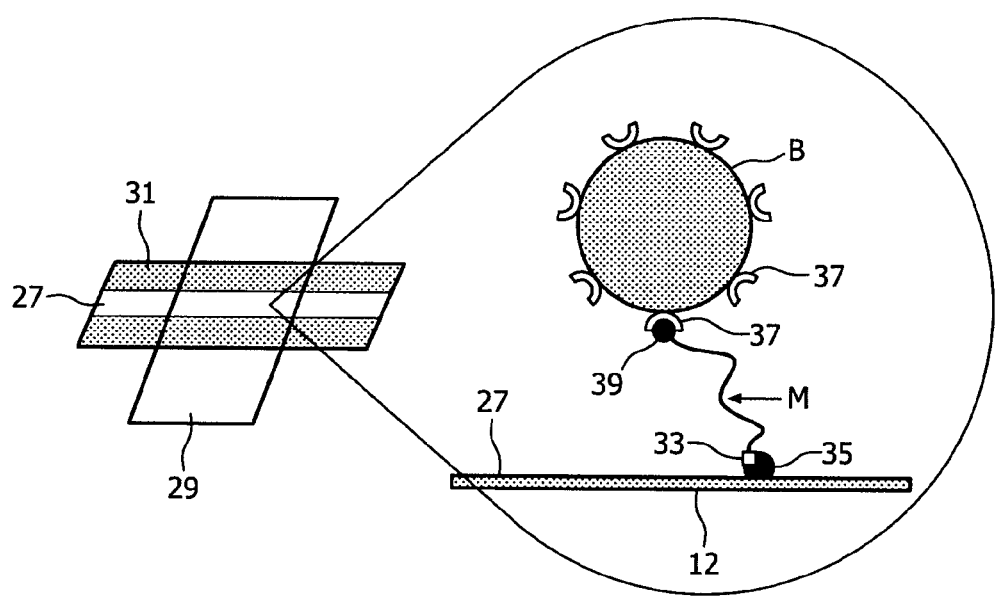

A sample 9, e.g. a simple flow cell may be made by separating a cover glass 27 (0.20×25×25 mm fused quarts Vitrosil 077®) and microscope slide 29 (1×75×25 mm fused quarts Vitrosil 077) with a layer of parafilm 31 (See FIGS. 2a and 2b). A plurality of molecules e.g. DNA molecules (1000 bps) M are at one end attached (e.g. tethered) to the first surface 8 via a first connector e.g. a dig 33 connecting to a second connector e.g. anti-dig 35. The other end of the molecule M may be attached (e.g. tethered) to a microbead B of a plurality of microbeads via a third connector e.g. biotin 39 binding with a fourth connector e.g. streptavadin 37.

The sample may also be prepared from a flow cell that is made out of one piece of material with a channel in the middle. A plurality of molecules e.g. DNA molecules (1000 bps) may be at one end attached (e.g. tethered) to a first surface of the channel and via a first connector e.g. a dig connected to a second connector e.g. anti-dig. The other end of the molecule may be attached (e.g. tethered) to a microbead of a plurality of microbeads via a third connector e.g. biotin binding with a fourth connector e.g. streptavidin. The flow cell may be provided with the molecules, the first, second, third and fourth connector and the beads by flowing them through the flow channel and let them react in the channel to prepare the sample. An advantage of using a flow cell made out of one piece is that it is more rigid and therefore acoustically a better resonance may be present increasing the forces that may be exerted on the beads.

The sample prepared from a flow cell made out of one piece of material with a channel in the middle may also be provided with the vibration generator e.g. the piezo element mounted on the sample. In this way we prepare a lab on chip design. To prevent sticking of the DNA, the surface of the flow cell may be coated with casein. The microbead B tethered to the DNA molecule may serve a double purpose: first as a handle to apply a force 25 to the DNA with the acoustic wave 13 and second as a probe to detect the DNA's response to that applied force 25. The physical property of the DNA molecules M may be determined by detecting the position of the microbead B in 3 dimensions over time with the detector device comprising objective 11 and camera 23 (in FIG. 1) and in response to the force 25 generated by the acoustic wave 13. The microbeads B and molecules M may be surrounded by water in the sample 9. An advantage of the apparatus is that it may be used with a large number of different microbeads. In magnetic manipulation apparatus one may be bound to the use of magnetic microbeads whereas in our system there is more freedom of the used microbeads of different materials.

We may also investigate direct protein-antibody interactions in the sample. In that case there may be a direct connection between the streptavidin 37 and the anti-dig 35 of FIG. 2b without the molecule "M", the biotin 39 and the dig 33 of FIG. 2b. The later being helpful if direct interactions are being investigated.

The center position of the microbead B may be calculated by the computer 24 for every image of the detector 23 to track the end-to-end length of the DNA molecule M over time. Since the size of the microbead B may be in the order of a wavelength the point spread function (PSF) may be imaged on the detector 23. To detect the center of the PSF (x, y) a cross correlation algorithm may be used, that achieves sub pixel resolution even when the PSF center is not more than a few pixels. Although a single measurement of the microbead position may directly yield information on the state of the DNA, multiple measurements may lead to a distribution that may be used to investigate the physical properties of the DNA molecule e.g. the length as well as length changes (for example induced by proteins). A typical value that describes the size of the distribution in relation to the average positions x and y may be the root mean square motion (RMS) and is given by equation 1.1.

$$((x-\overline{x})^2 + (y-\overline{y})^2)^{1/2} \tag{1.1}$$

In addition to the position of the microbead in x and y, the changes in height of the microbead (z) may also be recorded. And in contrast to the x, y position, the microbead's height may be a direct measurement of the DNA's length. The height may be determined by determining the shape of the PSF that is dependent on the distance from the sample to the detector or to calculate a z position of the microbead by the interference pattern image caused by an unfocused microbead. Hence, a change in height of the microbead leads to a change in the PSF. In order to relate the measured PSF to the changes in height, a look up table may be used (LUT, a library that contains the radial profile as a function of the microbeads height). The LUTs may be made by moving the sample over a known distance, using a piezo stage, and storing the radial profile of the microbead. To obtain the changes in height during a measurement, the measured radial profile may be compared to the profiles stored in the LUT. By interpolating between and averaging over multiple radial profiles, a detection accuracy of <5 nm may be achieved at an effective frame rate of 25 Hz.

To maximize the exerted force and minimize the amount of energy in the acoustic wave necessary to achieve desirable forces, selecting the proper material and microbead size may be very important. The microbeads may therefore be made of thermoplastics and thermosetting polymers or silica. Double stranded DNA starts to melt and convert into single stranded molecules at a force of around 65 piconewtons (pN) (depending on salt concentrations). Therefore, the molecular manipulation system may ideally be able to achieve forces of several tens of piconewtons to be able to fully stretch double stranded DNA.

FIG. 3 discloses a molecular manipulation system according to an embodiment. The system is constructed and arranged to have the first surface 8 in the sample holder perpendicular to the propagation direction of a standing wave generated with the acoustic wave generator 5 e.g. a piëzo element. The acoustic wave generator 5 has a vibration actuating plane 41 perpendicular to the propagation direction of the standing wave, the system being constructed and arranged to have the vibration actuation plane 41 substantially parallel to the first surface 8 in the sample holder 10.

The sample holder 10 may comprise a flow cell having a channel 43 with the first surface 8 along the inside of the channel 43. The acoustic wave may be used to exert a force on the microbeads B stretching the molecules M towards a centerline 45 of the channel 43 when activated. The acoustic wave may create a standing wave pushing the beads B away form the first surface 8 in the sample towards the centerline 45. A reflector 47 may be provided for illumination of the beads B. The reflector 47 may be provided between the sample holder 10 and the molecular manipulation device 5, which together may form a single unit. Illumination may be provided from a direction as depicted by arrow 49.

Alternatively, the sample holder may be a container holder for holding a replaceable container e.g. a petri dish with the surface provided with the sample perpendicular to the propagation direction of the standing wave in the standing wave. In this embodiment it is rather easy to replace the container with another container.

FIG. 4a depicts the X, Y movements of the microbeads when the microbeads are freely moving FM and moving with a 6.630 MHz acoustic standing wave AM.

FIG. 4b depicts the X, Y movements of the microbeads FM when the beads are freely moving and when an acoustic wave of 9.567 MHz is provided which is resonating, but this frequency is not favorable for pushing. Thereby streaming is dominant, in the flow channel which presses the molecules along the first surface. Clearly visible is the influence of an acoustic wave on the movements of the microbeads.

The detector device to detect a position of the microbead may also be a detector to detect a position of multiple microbeads that are connected in the sample to multiple molecules. By quantitive analysis of the microbeads and their position in the sample the apparatus may become very sensitive for detecting concentrations of a particular molecule in the sample and/or for detecting the influence of certain proteins on the length of the molecules. The apparatus may also be used to measure the presents and or concentration of particular molecules interacting with the molecules that are located between the cover glass and the microbead.

While specific embodiments of the invention have been described above, it will be appreciated that the invention may be practiced otherwise than as described. For example, the invention may take the form of a computer program containing one or more sequences of machine-readable instructions describing a method as disclosed above, or a data storage medium (e.g. semiconductor memory, magnetic or optical disk) having such a computer program stored therein.

The descriptions above are intended to be illustrative, not limiting. Thus, it will be apparent to one skilled in the art that modifications may be made to the invention as described without departing from the scope of the claims set out below.

The invention claimed is:

1. A molecular manipulation system for investigating molecules, the system comprising:
   a flow cell formed from one piece of material; and
   an acoustic wave generator,
   wherein the acoustic wave generator is integrated with the flow cell to form a single unit,
   wherein the flow cell defines a flow channel extending through the one piece of material,
   wherein the flow channel is defined by a plurality of channel surfaces of the one piece of material comprising a first channel surface and a second channel surface opposite the first channel surface,
   wherein the first channel surface in the flow channel comprises connectors to attach molecules in a sample to the first channel surface, and
   wherein the acoustic wave generator is configured to generate acoustic waves into the sample in the flow channel with a frequency tuned in accordance with a dimension across the flow channel to form a standing acoustic wave resonating between the first channel surface and the second channel surface of the one piece of material in order for the standing acoustic wave to exert a force of more than one piconewton on the molecules in the sample attached to the first channel surface in a direction away from the first channel surface.

2. The molecular manipulation system according to claim 1, wherein the system is configured to exert forces of 65 piconewtons on the molecules in the sample attached to the first channel surface.

3. The molecular manipulation system according to claim 1, further comprising an imaging detector configured to detect a response of the molecules connected to the first channel surface in order to determine the force exerted by the acoustic wave on the molecules.

4. The molecular manipulation system according to claim 3, wherein the imaging detector comprises a microscope, and wherein the system is configured so that a focal plane of the microscope is substantially parallel and slightly above the first channel surface in order to detect the molecules attached to the first channel surface.

5. The molecular manipulation system according to claim 3, wherein the imaging detector is configured to produce a digital image of a focal plane and the system comprises a calculation device configured to calculate a position of the molecules in a direction perpendicular to the focal plane by processing of an interference pattern caused by molecules which are not in focus.

6. The molecular manipulation system according to claim 3, wherein the imaging detector is configured to produce a digital image of a focal plane and the system comprises a calculation device to calculate a position of the molecules in a direction parallel to the focal plane.

7. The molecular manipulation system according to claim 3, wherein the imaging detector is configured to produce a digital image of a focal plane and the system comprises a processing device configured to provide a quantitative analysis of the molecules in the sample based on the digital image.

8. The molecular manipulation system according to claim 3, wherein the system comprises an illumination system configured to illuminate the sample in the flow cell.

9. The molecular manipulation system according to claim 8, further comprising an illumination reflector between the flow cell and the acoustic wave generator.

10. The molecular manipulation system according to claim 1, wherein the acoustic wave generator is configured for adjustable frequency.

11. The molecular manipulation system according to claim 1, wherein the first channel surface and the second channel surface are perpendicular to a propagation direction of the acoustic waves generated by the acoustic wave generator into the sample.

12. The molecular manipulation system according to claim 1, wherein the acoustic wave generator defines a vibration actuating plane perpendicular to a propagation direction of the acoustic waves, and wherein the vibration actuation plane is substantially parallel to the first and second channel surfaces.

13. The molecular manipulation system according to claim 1, wherein the connectors provided on the first channel surface comprise a dig or anti-dig and are configured to connect with an anti-dig or dig, respectively, provided on the molecules.

14. A method of investigating molecules, the method comprising:
   attaching a sample with molecules to the first channel surface of the molecular manipulation system of claim 1;
   generating acoustic waves into the sample in the flow channel with a frequency tuned in accordance with a dimension across the flow channel to form a standing acoustic wave resonating between the first channel surface and the second channel surface, wherein the standing acoustic wave exert a force of more than one piconewton on the molecules in the sample attached to the first channel surface in a direction away from the first channel surface provided with the connectors; and
   detecting a response of the molecules attached to the first channel surface to the force exerted by the acoustic wave to investigate the molecules.

* * * * *